United States Patent

Magagnoli et al.

[11] 3,996,253
[45] Dec. 7, 1976

[54] PROCESS FOR THE PREPARATION OF COLOR IMAGES

[75] Inventors: Remo Magagnoli, Ferrania (Savona); Enzo Coraluppi, Bologna, both of Italy

[73] Assignee: Minnesota Mining and Manufacturing Company, St. Paul, Minn.

[22] Filed: Jan. 7, 1971

[21] Appl. No.: 104,754

Related U.S. Application Data

[62] Division of Ser. No. 519,965, Jan. 11, 1966, Pat. No. 3,446,622.

[52] U.S. Cl. .................. 260/397.7 D; 260/519; 260/553 C
[51] Int. Cl.$^2$ ............................ C07C 127/19
[58] Field of Search ............. 260/519, 553 C, 397.7

[56] References Cited
OTHER PUBLICATIONS

Chem. Abs. vol. 63, Subject Index, p. 633S (1965).

Chem. Abs. vol. 63, Formula Index, pp. 503F, 555F (1965).
The Naming and Indexing of Chem. Cpds. from Chem. Abs., (A.C.S., Easton, Pa., 1962) pp. 87N–88N.
Hackhs Chem. Dict. (McGraw—Hill, N.Y., 1969), pp. 25, 26, 35.

*Primary Examiner*—Henry R. Jiles
*Assistant Examiner*—C. M. S Jaisle
*Attorney, Agent, or Firm*—Alexander, Sell, Steldt & Delahunt

[57] ABSTRACT

A photographic color coupler consisting of a phenolic compound having in the 2-position the radical

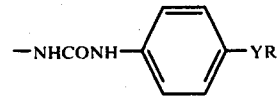

wherein Y is an amide or a sulfonamide bridging radical and wherein R is aryl or alkyl.

12 Claims, No Drawings

PROCESS FOR THE PREPARATION OF COLOR IMAGES

This is a division of application Ser. No. 519,965 which was filed Jan. 11, 1966, now U.S. Pat. No. 3,446,622.

This invention relates to a process for the preparation of color images, particularly of blue-green photographic images, and to photographic materials useful in this process.

For the preparation of blue-green photographic images alpha-naphtholic and phenolic color formers have been known to be useful. Generally these color formers have had substituents in the 2 or 3 position to the hydroxyl group, e.g. carbonamido, acylamino, sulphonamido or sulphonacylamino substituents. The naphtholic color formers have been preferred, since the phenolic color formers tend to produce dyes which are not satisfactorily stable to light and which tend to yellow upon aging due to residual color former.

In German Pat. No. 1,163,144 (Nov. 11, 1962) the 2-ureido phenols disclosed as color formers for cyan dyes are not subject to the light stability problems generally associated with phenolic cyan color formers. However, the dyes produced by chromogenic development generally have an absorption maximum in the shorter wavelength region of the spectrum, e.g. in the range of 610 to 640 millimicrons, normally below about 645 millimicrons, and are accordingly not considered desirable for conventional subtractive color photography, in which cyan dyes having absorption maxima of at least 645 are preferred.

It has now been found that certain derivatives of 2-ureido phenols are suitable for producing cyan dye images in a photographic film upon reaction with the oxidation products of a chromogen developer, such as p-diethylamino-aniline, and that the resulting cyan dyes are light stable and have an absorption in the desired portion of the light spectrum for a trichromic subtractive color film and process. These 2-ureido phenols have, in the 2-position, a substituent of the formula

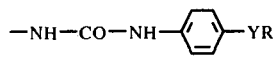

wherein Y is —NHCO—, —CONH—, —NHSO$_2$—, or —SO$_2$NH— and R is hydrogen, an aryl group, an arylaliphatic group or an aliphatic group. In the accompanying Table the color formers of German Pat. No. 1,163,144 are compared to the color formers of this invention, and the improved maximum absorption of the latter is shown. The color couplers appearing in the Table (Nos. I to XVIII) are prepared as follows:

Coupler I 10.9 g. of o-aminophenol was dissolved in dioxane. 21.75 g. of p-isocyano benzene sulphonyl chloride was added to the hot solution, which was then refluxed for one hour and poured into a boiling solution of 7.45 g. of aniline in dioxane and pyridine. After crystallization from ethanol-water 36 g. of product, M.P. 203°–205° C., was separated.

Coupler II 2.43 g. of 2-[p'-aminophenyl] ureidophenol was dispersed in dioxane and pyridine, then, 1.4 g. of benzoyl-chloride were added to the mixture. The solution was refluxed and separated from any tar, and was thereafter poured into diluted hydrochloric acid. 3.5 g. of product was obtained, which was purified with an alcohol-water solution until a product melting at 190° C. was obtained.

2-[p'-aminophenyl] ureidophenol (M.P. 200° C.) was prepared by reducing with hydrogen an alcoholic solution of the nitro-derivative at room temperature using a palladium on carbon catalyst (10% Pd). The nitro-derivative, i.e. 2-[p'-nitrophenyl] ureidophenol, was obtained by dissolving 10.9 g. of o-aminophenol in dioxane and adding 16.4 g. of p-nitrophenylisocyanate to the dioxane solution at 15°–16° C. After purification from ethanol-water 25 g. of the nitro-derivative (M.P. 213°–215° C.) was separated.

Coupler III 2.43 g. of 2-[p'-aminophenyl] ureidophenol was diluted in pyridine and 1.9 g. of p-toluene sulphonyl chloride was added to the solution, which then was refluxed for one hour and was mixed with diluted nydrochloric acid. 3.6 g. of product was obtained which was purified from ethanol-water. Its melting point was at 183°–186° C.

Coupler IV

The procedure was the same as in Coupler I, but using 2-amino-4-chlorophenol instead of o-aminophenol. A product with M.P. 205°–207° C. was obtained.

Coupler V

The procedure was the same as in Coupler I, but replacing o-amino-phenol with 2-amino-5-methylphenol. After purification, a product with M.P. at 192°–193° C, was obtained.

Coupler VI

It was prepared in the same manner as Coupler I, using 2-amino-5-methyl-4,6-dichlorophenol instead of o-aminophenol. The product obtained had M.P. 232°–234° C.

Coupler VII 10.9 g. of o-aminophenol was added to dioxane, and 21.75 g. of p-isocyano benzene sulphonyl chloride was added to the boiling solution, which then was refluxed for one hour. This solution was poured into another boiling solution of 24.83 g. of p-dodecylaniline in dioxane and pyridine. 50 g. of product separated. After washing with benzene it had M.P. 141°–144° C.

Coupler VIII

The procedure is the same as for Coupler VII, but in this case p-dodecylaniline was substituted with 3-amino-5-stearoylaminobenzoic acid. 63 g. of product separated by crystallizing from acetonitrile. The melting point was 154°–158° C.

Coupler IX 2.43 g. of 2-[p'-aminophenyl] ureidophenol was dispersed in dioxane. 2.39 g. of m-chlorosulphobenzoyl-chloride was added and the mixture was refluxed for 1 hour. The solution was then poured into a boiling solution of 3.76 g. of 3-amino-5-stearoylaminobenzoic acid in dioxane and pyridine. After purification with acetone and light petroleum (40°–70° C.), a product having M.P. 158°–162° C., was separated.

Coupler X 2.43 g. of 2-[p'-aminophenyl] ureidophenol were dispersed in dioxane and pyridine. 6.21 g. of 3-chlorosulpho(3'-carboxy-5'-stearoylamino) benzanilide was added to the dispersion at room temperature. A solution was obtained after refluxing the dispersion for 1 hour. The solution was then poured into dilute hydrochloric acid. 7.6 g. of product were purified with acetone and light petroleum (40°–70° C.). M.P. 160°–164° C.

3-chlorosulpho-(3'-carboxy-5'-stearoylamino) benzanilide was prepared by heating to boiling a solution of 3-amino-5-stearoylamino-benzoic acid in acetone. To the solution was added a m-chlorosulphobenzoyl chloride, and the mixture was refluxed for 1 hour. After it was washed with acetone a product having M.P. 198°–200° C. was obtained.

Coupler XI

The procedure was the same as in Coupler VIII, substituting 2-amino-4-chlorophenol for o-aminophenol. A product was obtained having M.P. 168°–169° C.

Coupler XII

The procedure was similar to the preparation of Coupler VIII, substituting 2-amino-4-chlorophenol for o-aminophenol. After purification from ethanol and acetonitrile a product was obtained with M.P. at 174°–175° C.

Coupler XIII 12.3 g. of 2-amino-5-methylphenol was diluted in dioxane. 21.7 g. of p-isocyano benzene sulfonyl chloride were added to the hot solution, which was then refluxed for 1 hour. Then the solution was poured into a boiling solution of 20.2 g. of tetradecylamine in dioxane and pyridine. 50 g. of product, having, after crystallization from acetonitrile, M.P. 148°–152° C., was separated.

Coupler XIV

The procedure was the same as in Coupler VII, substituting 2-amino-5-methylphenol for o-aminophenol. After purification with benzol and light petroleum (40°–70° C.) a product was obtained with M.P. 122°–124° C.

Coupler XV

The procedure was the same as Coupler VIII, substituting 2-amino-5-methylphenol for o-aminophenol. A product was obtained with M.P. 162°–164° C.

Coupler XVI

The procedure was the same as Coupler XIII, substituting 2-amino-5-methyl-4,6-dichlorophenol for o-aminophenol; M.P. 126°–130° C.

Coupler XVII

The procedure was the same as Coupler VII, using 2-amino-5-methyl-4,6-dichlorophenol instead of aminophenol. After crystallization from acetonitrile, a product with M.P. 193°–195° C. was obtained.

Coupler XVIII

The procedure was the same as Coupler VIII, substituting 2-amino-5-methyl-4,6-dichlorophenol for o-aminophenol. M.P. 147°–167° C.

All the above described compounds can be used for producing color photographic images, by the color development process as illustrated in the following examples.

EXAMPLE 1

A sample photographic element containing a layer of gelatino-silver halide emulsion was exposed and then processed in a color developing bath of the following composition:

Sodium carbonate, anhydrous — 20 g.
Sodium sulphite, anhydrous — 0.5 g.
N,N-diethyl-p-phenylendiamine sulphate — 1 g.
Coupler I — 1 g.
Water to make — 1000 cc.

The developed material was washed, then processed in a bleaching bath, washed, fixed, washed again and dried. A cyan color image, due to the formation of a dye with maximum absorption at 668 m$\mu$ was obtained.

Similarly, if in the composition of a developing bath, Coupler I is substituted by Coupler II, III, IV, V, and VI, cyan images are obtained containing dyes with maximum absorptions at 657, 662, 680, 655 and 695 m$\mu$, respectively.

In the same way, dyes with maximum absorption at 650, 630, 640 and 672 m$\mu$ respectively are obtained from compound 1,2,3 and 4 referred to in the first column of the Table.

EXAMPLE 2

A solution made of 10 g. of Coupler VIII, 20 cc. of methanol, and 15 cc. of 2N NaOH solution and 250 cc. of water was prepared. This solution was added, according to the normal technique, to 1 Kg. of silver halide photographic emulsion, which was then coated onto a base. The photosensitive material so obtained was exposed and then developed in a N,N-diethyl-p-phenylenediamine color developing bath.

After bleaching and fixing, an image of the blue green dye with maximum absorption at .655 m$\mu$, formed in the exposed areas.

Similarly, Couplers VII, IX, X, XI, XII, XIII, XIV, XV, XVI, XVII, and XVIII can be used to produce dyes with maximum absorption at 667, 655, 652, 668, 658, 648, 655, 640, 656, 668, 652 m$\mu$, respectively.

Compounds 5, 6, 7 and 8 of the first column of the Table form dyes with maximum absorption at 627, 630, 618 and 608 m$\mu$, respectively.

EXAMPLE 3

Couplers VII, XI, XIII and XVI were also used in the following manner.

10 g. of the coupler was added at 50° C. to 20 cc. of dibutyl-phthalate and 60 cc. of ethyl acetate.

This solution was added to 200 cc. of a 4% solution of inert gelatine containing also 10 cc. of Tergitol 4 (tetradecyl-sodium sulphonate). This mixture was poured into a homogenizer and the resulting homogenized dispersion was added to 1 Kg. of silver halide photographic emulsion, which was then coated onto a base. The photosensitive material so obtained was exposed and then developed in a N,N-diethyl-p-phenylene-diamine color developing bath. After bleaching and fixing a blue-green image formed in the exposed parts. This image is due to the formation of dye having maximum absorption as indicated in Example 2.

The above data illustrates the outstanding results achieved with 2-ureido phenols having a p-substituted phenyl group of the formula—$C_6H_4YR$, where Y and R are defined above. Preferably R is phenyl (including substituted phenyl), aliphatic (e.g. alkyl), phenylaliphatic (e.g. alkylamidophenyl) or phenylarylaliphatic (e.g. alkylamidocarbanilinophenyl).

Various other embodiments of the present invention will be apparent to those skilled in the art without departing from the scope thereof.

TABLE

| No. | Color Formers of German Patent No. 1,163,144 | Max. Absorp. mμ | No. | Color Formers of This Invention | Max. Absorp. mμ |
|---|---|---|---|---|---|
| 1 | OH–⟨⟩–NH–CO–NH–⟨⟩ | 650 | I | OH–⟨⟩–NH–CO–NH–⟨⟩–SO₂NH–⟨⟩ | 668 |
| | | | II | OH–⟨⟩–NH–CO–NH–⟨⟩–NH–CO–⟨⟩ | 657 |
| | | | III | OH–⟨⟩–NH–CO–NH–⟨⟩–NH–SO₂–⟨⟩–CH₃ | 662 |
| 2 | OH, Cl–⟨⟩–NH–CO–NH–⟨⟩ | 630 | IV | OH, Cl–⟨⟩–NH–CO–NH–⟨⟩–SO₂NH–⟨⟩ | 680 |
| 3 | OH, CH₃–⟨⟩–NH–CO–NH–⟨⟩ | 640 | V | OH, CH₃–⟨⟩–NH–CO–NH–⟨⟩–SO₂NH–⟨⟩ | 655 |
| 4 | OH, Cl, CH₃, Cl–⟨⟩–NH–CO–NH–⟨⟩ | 672 | VI | OH, Cl, CH₃, Cl–⟨⟩–NH–CO–NH–⟨⟩–SO₂NH–⟨⟩ | 695 |
| 5 | OH–⟨⟩–NH–CO–NH–C₁₄H₂₉ | 627 | VII | OH–⟨⟩–NH–CO–NH–⟨⟩–SO₂NH–⟨⟩–C₁₂H₂₅ | 667 |
| | | | VIII | OH–⟨⟩–NH–CO–NH–⟨⟩– ; –SO₂NH–⟨COOH, NH–CO–C₁₇H₃₃⟩ | 655 |
| | | | IX | OH–⟨⟩–NH–CO–NH–⟨⟩– ; –NH–CO–⟨⟩–SO₂NH–⟨COOH, NH–CO–C₁₇H₃₃⟩ | 655 |
| | | | X | OH–⟨⟩–NH–CO–NH–⟨⟩– ; –NH–SO₂–⟨⟩–CO–NH–⟨COOH, NH–CO–C₁₇H₃₃⟩ | 652 |

TABLE-continued

| No. | Color Formers of German Patent No. 1,163,144 | Max. Absorp. m$\mu$ | No. | Color Formers of This Invention | Max. Absorp. m$\mu$ |
|---|---|---|---|---|---|
| 6 | (OH, Cl)-phenyl-NH—CO—NH—$C_{14}H_{29}$ | 650 | XI | (OH, Cl)-phenyl-NH—CO—NH-phenyl-$SO_2NH$-phenyl-$C_{12}H_{23}$ | 668 |
| | | | XII | (OH, Cl)-phenyl-NH—CO—NH-phenyl, with —$SO_2NH$-phenyl(COOH)(NH—CO—$C_{17}H_{33}$) | 658 |
| 7 | (OH, $CH_3$)-phenyl-NH—CO—NH—$C_{14}H_{29}$ | 618 | XIII | ($H_3C$, OH)-phenyl-NH—CO—NH-phenyl-$SO_2NH$—$C_{14}H_{29}$ | 648 |
| | | | XIV | ($H_3C$, OH)-phenyl-NH—CO—NH-phenyl, —$SO_2NH$-phenyl-$C_{12}H_{25}$ | 655 |
| | | | XV | ($H_3C$, OH)-phenyl-NH—CO—NH-phenyl, —$SO_2NH$-phenyl(COOH)(NH—CO—$C_{17}H_{25}$) | 640 |
| 8 | ($H_3C$, Cl, OH, Cl)-phenyl-NH—CO—NH—$C_{14}H_{29}$ | 608 | XVI | (Cl, $CH_3$, OH, Cl)-phenyl-NH—CO—NH-phenyl-$SO_2NH$—$C_{14}H_{29}$ | 656 |
| | | | XVII | (Cl, $H_3C$, OH, Cl)-phenyl-NH—CO—NH-phenyl, —$SO_2NH$-phenyl-$C_{12}H_{25}$ | 668 |
| | | | XVIII | (Cl, $CH_3$, OH, Cl)-phenyl-NH—CO—NH-phenyl, —$SO_2NH$-phenyl(COOH)(NH—CO—$C_{17}H_{33}$) | 652 |

What is claimed is:

1. A phenolic photographic color coupler having a phenolic nucleus capable of reacting with the oxidation product of a chromogen developer to form a dye, said coupler having bonded in the 2-position of the phenolic nucleus a radical of the formula

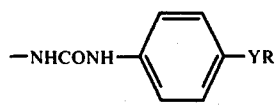

wherein Y is —CONH—, —NHSO$_2$— or —SO$_2$NH— and R is an aryl group or an aralkyl group.

2. The photographic color coupler of claim 1 in which R is a phenyl group.

3. The photographic color coupler of claim 1 in which R is an alkylphenyl group.

4. The photographic color coupler of claim 1 in which R is carboxyphenyl.

5. The photographic color coupler of claim 1 in which R is an alkylamidophenyl group.

6. The photographic color coupler of claim 1 in which R is alkyl amidoanilidophenyl.

7. A photographic color coupler of the formula

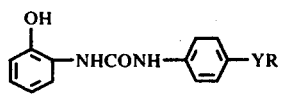

wherein the phenolic nucleus of said compound may have up to 3 substituents selected independently from lower alkyl and halogen, wherein Y is —CONH—, —NHSO$_2$—, or —SO$_2$NH—, and wherein R is phenyl, alkylphenyl, alkamidophenyl, (3-carboxy-5-alkamido)-phenyl, [2-(2'-carboxy-4'-alkamido)-phenylcarbamoyl], and [2-(2'-carboxy-4'-alkamido)-phenylsulfamoyl].

8. The photographic color coupler of claim 7 having the formula

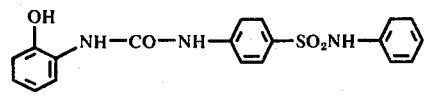

9. A color coupler of the formula

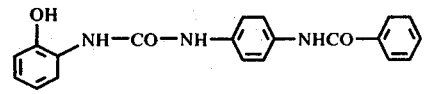

10. The photographic color coupler of claim 7 having the formula

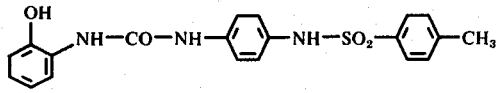

11. The photographic color coupler of claim 7 having the formula

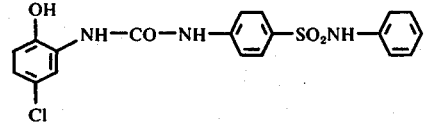

12. The photographic color coupler of claim 7 having the formula

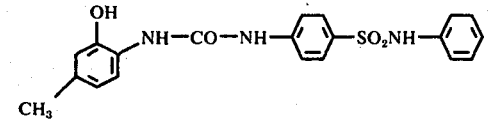

* * * * *

UNITED STATES PATENT AND TRADEMARK OFFICE
CERTIFICATE OF CORRECTION

PATENT NO. : 3,996,253
DATED : December 7, 1976
INVENTOR(S) : Remo Magagnoli and Enzo Coraluppi It is certified that error appears in the above-identified patent and that said Letters Patent are hereby corrected as shown below:

Column 2, line 21, "nydrochloric" should be --hydrochloric--.

Column 4, line 40, ".655 mµ" should be --655 mµ--.

Signed and Sealed this

Twelfth Day of April 1977

[SEAL]

Attest:

RUTH C. MASON
*Attesting Officer*

C. MARSHALL DANN
*Commissioner of Patents and Trademarks*